(12) United States Patent
Nakano et al.

(10) Patent No.: US 9,976,976 B2
(45) Date of Patent: May 22, 2018

(54) GAS SENSOR APPARATUS AND INSTALLATION STRUCTURE OF GAS SENSOR APPARATUS

(71) Applicant: Hitachi Automotive Systems, Ltd., Hitachinaka-shi, Ibaraki (JP)

(72) Inventors: Hiroshi Nakano, Tokyo (JP); Masahiro Matsumoto, Tokyo (JP); Satoshi Asano, Tokyo (JP); Shinobu Tashiro, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 88 days.

(21) Appl. No.: 14/899,175

(22) PCT Filed: Feb. 3, 2014

(86) PCT No.: PCT/JP2014/052380
§ 371 (c)(1),
(2) Date: Dec. 17, 2015

(87) PCT Pub. No.: WO2014/203553
PCT Pub. Date: Dec. 24, 2014

(65) Prior Publication Data
US 2016/0139071 A1    May 19, 2016

(30) Foreign Application Priority Data
Jun. 21, 2013 (JP) .................. 2013-130704

(51) Int. Cl.
*G01N 27/12* (2006.01)
*G01N 27/18* (2006.01)
(Continued)

(52) U.S. Cl.
CPC ......... *G01N 27/18* (2013.01); *F02M 35/1038* (2013.01); *F02M 35/10386* (2013.01);
(Continued)

(58) Field of Classification Search
CPC .................................................. G01N 27/407
(Continued)

(56) References Cited

U.S. PATENT DOCUMENTS

| 5,505,073 A * | 4/1996 | Gerblinger ......... G01N 33/0009 73/31.05 |
| 6,361,206 B1 * | 3/2002 | Bonne ................... G01F 1/6842 374/135 |

(Continued)

FOREIGN PATENT DOCUMENTS

| JP | 7-151723 A | 6/1995 |
| JP | 2002-535675 A | 10/2002 |

(Continued)

OTHER PUBLICATIONS

International Search Report (PCT/ISA/210) issued in PCT Application No. PCT/JP2014/052380 dated Mar. 25, 2014 with English-language translation (four (2) pages).*

(Continued)

*Primary Examiner* — Clayton E LaBalle
*Assistant Examiner* — Kevin Butler
(74) *Attorney, Agent, or Firm* — Crowell & Moring LLP

(57) ABSTRACT

To provide a gas sensor apparatus capable of preventing clogging of a gas intake port due to particles, droplets, or the like, of a gas and maintaining measurement accuracy for a long time, a gas sensor apparatus 1 includes a housing 3. The housing 3 includes an expansion chamber 6 communicating with an air intake passage 2 via an air intake port 8, and a measurement chamber 5 communicating with the expansion chamber 6 via a communicating portion 7. A double squeezing structure including the gas intake port 8 and the communicating portion 7 is provided, and two stages of regions where the volume expands between the gas intake port 8 and the measurement chamber 5 are provided. As a result, the (Continued)

EMBODIMENT 1 movement of the air in the measurement chamber 5 is decreased. It is possible to provide a structure in which the capacity of the gas intake port 8 is increased to avoid clogging of the gas intake port due to particles or droplets.

13 Claims, 20 Drawing Sheets

(51) Int. Cl.
| | |
|---|---|
| *G01K 13/02* | (2006.01) |
| *G01N 33/00* | (2006.01) |
| *G01F 1/684* | (2006.01) |
| *F02M 35/10* | (2006.01) |
| *G01D 11/24* | (2006.01) |
| *G01F 1/692* | (2006.01) |
| *G01N 27/407* | (2006.01) |
| *G01N 1/22* | (2006.01) |
| *G01M 15/10* | (2006.01) |
| *G01N 9/36* | (2006.01) |
| *F02D 41/18* | (2006.01) |

(52) U.S. Cl.
CPC ............ *G01D 11/245* (2013.01); *G01F 1/684* (2013.01); *G01F 1/6842* (2013.01); *G01F 1/692* (2013.01); *G01K 13/02* (2013.01); *G01N 27/121* (2013.01); *G01N 33/0016* (2013.01); *F02D 41/18* (2013.01); *F02D 2200/0414* (2013.01); *F02D 2200/0418* (2013.01); *G01K 2013/024* (2013.01); *G01K 2205/04* (2013.01); *G01M 15/102* (2013.01); *G01N 1/2252* (2013.01); *G01N 9/36* (2013.01); *G01N 27/12* (2013.01); *G01N 27/407* (2013.01); *G01N 27/4077* (2013.01)

(58) Field of Classification Search
USPC ........................................................ 73/23.31
See application file for complete search history.

(56) References Cited

U.S. PATENT DOCUMENTS

| | | | | |
|---|---|---|---|---|
| 2003/0094041 A1* | 5/2003 | Iwaki | ................... | G01F 1/6842 73/204.21 |
| 2012/0085324 A1* | 4/2012 | Saito | ................ | F02M 35/10393 123/494 |
| 2013/0167630 A1* | 7/2013 | Ueda | .................... | G01F 1/6842 73/198 |
| 2013/0192388 A1* | 8/2013 | Kono | .................... | G01F 1/6845 73/861.47 |
| 2016/0139071 A1* | 5/2016 | Nakano | ............ | F02M 35/10386 73/23.31 |
| 2016/0202200 A1* | 7/2016 | Nakano | .................. | G01N 27/18 73/23.31 |

FOREIGN PATENT DOCUMENTS

| | | | |
|---|---|---|---|
| JP | 2003-176740 A | 6/2003 | |
| JP | 2010-2197 A | 1/2010 | |
| JP | 2010-151795 A | 7/2010 | |
| JP | 2010151795 | * 7/2010 | |
| JP | 2012-58180 A | 3/2012 | |
| JP | 2012058180 | * 3/2012 | ............ G01N 27/18 |
| JP | 2012-83119 A | 4/2012 | |
| JP | 2012-112979 A | 6/2012 | |
| WO | WO 2012/014632 A1 | 2/2012 | |

OTHER PUBLICATIONS

Written Opinion International Search Authority (PCT/ISA/210) issued in PCT Application No. PCT/JP2014/052380 dated Jun. 21, 2013 with English-language translation (four (5) pages).*
International Search Report (PCT/ISA/210) issued in PCT Application No. PCT/JP2014/052380 dated Mar. 25, 2014 with English-language translation (four (4) pages).

* cited by examiner

EMBODIMENT 1

EMBODIMENT 1

EMBODIMENT 1

EMBODIMENT 1

EMBODIMENT 2

EMBODIMENT 3

EMBODIMENT 4

EMBODIMENT 5

EMBODIMENT 5

EMBODIMENT 5

EMBODIMENT 5

EMBODIMENT 6

EMBODIMENT 6

EMBODIMENT 6

EMBODIMENT 7

EMBODIMENT 7

EMBODIMENT 7

EMBODIMENT 8

EMBODIMENT 9

EMBODIMENT 10

GAS SENSOR APPARATUS AND INSTALLATION STRUCTURE OF GAS SENSOR APPARATUS

TECHNICAL FIELD

The present invention relates to a gas sensor apparatus including a concentration sensor element for detecting gas concentration, and also relates to an installation structure of such a gas sensor apparatus.

BACKGROUND ART

Gas sensor apparatuses that measure environmental characteristics, such as concentration and temperatures of a gas, are used in various technical fields. In the internal combustion engine for a vehicle, for example, an intake air amount and an intake air temperature are measured to optimize the fuel injection amount in order to reduce fuel consumption. For the optimal operation of the internal combustion engine, high accuracy measurement of environmental parameters of the concentration, such as temperatures and humidity, (which will simply be referred to as the concentration hereinafter) is required. The environmental sensor elements that measure temperatures and concentration are also used in the internal combustion engine for a hydrogen fuel.

When the environmental sensor elements are installed in an air intake passage of the internal combustion engine, air (gas) that flows through a main passage is partially taken into a sub-passage of a housing, and the concentration, such as humidity, is measured by the concentration sensor element stored in a measurement chamber that communicates with the sub-passage via a gas intake port. In this structure, the concentration sensor element, which measures the concentration, is not directly exposed to the air flow. As a result of this, a dust-proof effect, or an effect of reducing breakage of the sensor element due to collision of particles, can be obtained. When the concentration sensor element is disposed closer to a pipe wall than to the sub-passage, a temperature of the internal combustion engine increases and the temperature increase causes heat transmission from the internal combustion engine via a pipe wall. The measurement accuracy of the temperature is thus adversely affected. To prevent this, a gas sensor apparatus in which the measurement chamber is disposed closer to the center of the passage away from the passage wall of the main passage instead of the sub-passage is known (e.g., PTL 1).

CITATION LIST

Patent Literature

PTL 1: JP 2010-151795 A

SUMMARY OF INVENTION

Technical Problem

An air flow rate changes and pulsation of air increases in the air intake passage according to the operation conditions of the internal combustion engine. This causes fluctuations of the air taken into a measurement chamber and deteriorates detection accuracy. To prevent this, it is necessary to decrease the capacity of a gas intake port that leads to the measurement chamber. As the capacity of the gas intake port decreases, however, the problem of impairing the measurement accuracy may occur, because particles or droplets of oil, dust, or the like that are present in the air intake passage of the internal combustion engine are disposed on the peripheral side face of the gas intake port to clog the gas intake port. This causes a significant decrease in responsiveness and damages the measurement accuracy. In PTL 1, a thermal concentration sensor element is used as the concentration sensor element for the measurement of concentration. The thermal concentration sensor element uses a difference in thermal conductivity of gas according to the concentration of the gas. The thermal concentration sensor element measures the concentration based on variations of a resistance value generated from a difference in heat radiation amount radiated into the atmosphere from a heated resistor. In this type of sensor element, fluctuations of the air flow rate and the pulsation of the air taken into the measurement chamber are factors to deteriorate the detection accuracy.

Solution to Problem

A gas sensor element of the present invention includes
a supporting member,
a concentration sensor element having a detecting portion and fixed to the supporting member, and
a housing.
The housing includes
a first cavity portion at least covering a region of the supporting member where the concentration sensor element is fixed, and storing the concentration sensor element with the detecting portion being exposed,
a gas intake port that is opened externally,
a second cavity portion provided between the first cavity portion and the gas intake port, and
a communicating portion communicating the first cavity portion with the second cavity portion. An installation structure of a gas sensor apparatus of the present invention includes
a humidity sensor element,
a flow rate sensor element,
a supporting member supporting the humidity sensor element and the flow rate sensor element, and
a housing covering a region of the supporting member where the humidity sensor element is supported.
The housing includes
a gas sensor apparatus, and
an internal combustion engine.
The gas sensor apparatus includes
a first cavity portion storing the humidity sensor element,
a gas intake port,
a second cavity portion provided between the first cavity portion and an gas intake port, and
a communicating portion communicating the first cavity portion with the second cavity portion.
The gas sensor apparatus is installed in an air intake passage in the internal combustion engine.
The gas intake port of the gas sensor apparatus is formed in a side face of the housing approximately in parallel with a direction of gas flow flowing through the air intake passage, or in a side face on the rear side of the housing relative to the gas flowing through the air intake passage.
The flow rate sensor element is partitioned from the first cavity portion and the second cavity portion.

Advantageous Effects of Invention

According to embodiments of the present invention, a double squeezing structure including the gas intake port and the communicating portion is provided. A volume of the gas that flows into the passage from the gas intake port to the measurement chamber expands in two stages. Since the movement of the air in the measurement chamber is decreased, measurement accuracy can be maintained even when the capacity of the gas intake port is increased. Accordingly, clogging of the gas intake port due to particles or droplets contained in the gas can be reduced, and the responsiveness and detection accuracy can be maintained. Since the movement of the air in the first cavity portion that stores the concentration sensor element is suppressed, the decrease of the detection accuracy can be prevented even when the thermal concentration sensor element that is easily affected by the movement of the gas flow is used.

BRIEF DESCRIPTION OF DRAWING

FIGS. 3A and 3B illustrate a sensor package of FIG. 2, in which FIG. 3A is a plan view and FIG. 3B is a cross-sectional view of an internal structure.

FIGS. 4A-4C are used to explain a function and an effect of the gas sensor apparatus according to the embodiment, in which FIG. 4A is related to Embodiment 1, FIG. 4B is a modification of FIG. 4A, and FIG. 4C illustrates a past example.

FIGS. 11A and 11B are enlarged view of the sensor package illustrated in FIG. 8, in which FIG. 11A is an external perspective view and FIG. 11B is a plan view illustrating the internal structure.

DESCRIPTION OF EMBODIMENTS

Embodiment 1

Figure 1:
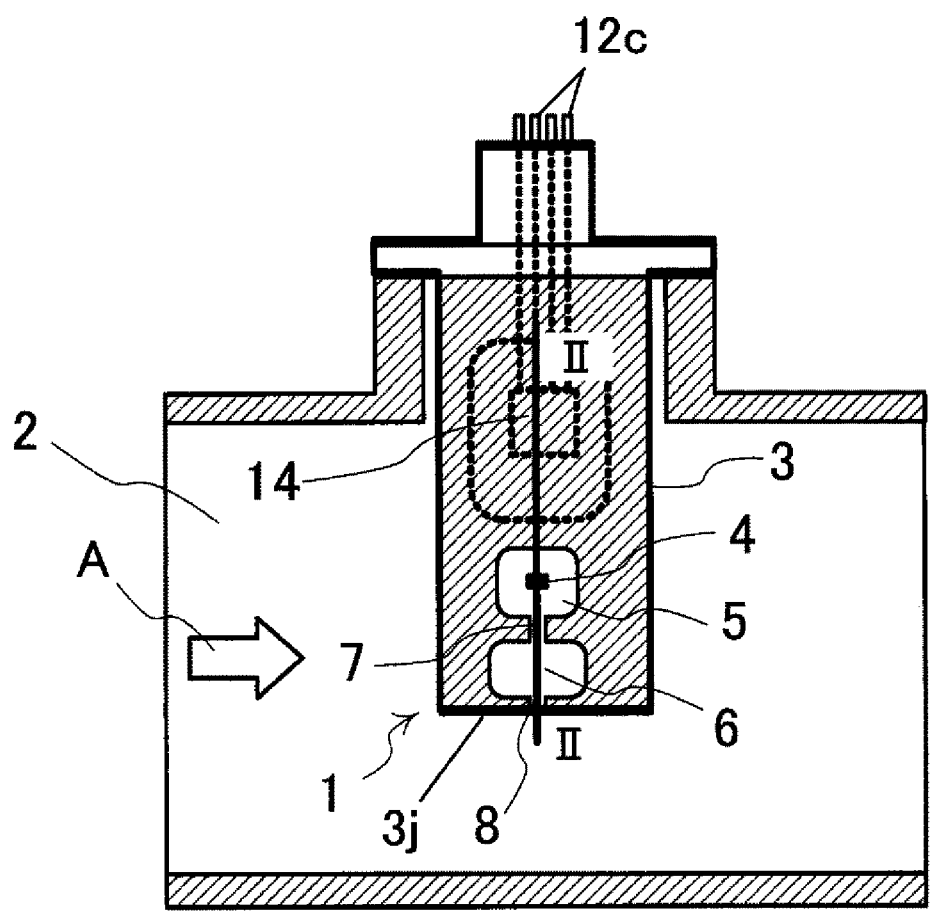
FIG. 1 is a cross-sectional view of a gas sensor apparatus and an installation structure of the gas sensor apparatus according to an embodiment of the present invention.
Figure 2:
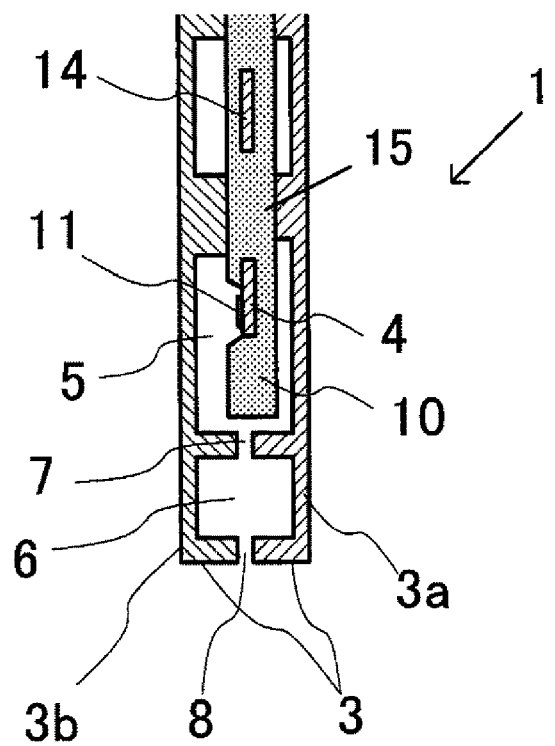
FIG. 2 is a cross-sectional view of the gas sensor apparatus of FIG. 1 cut along line II-II.
Figure 3A:
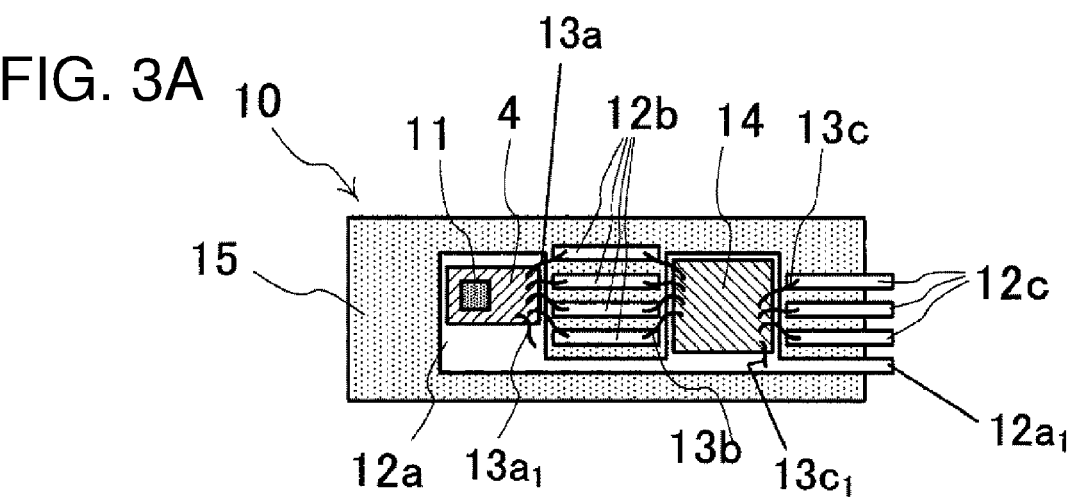
Figure 3B:
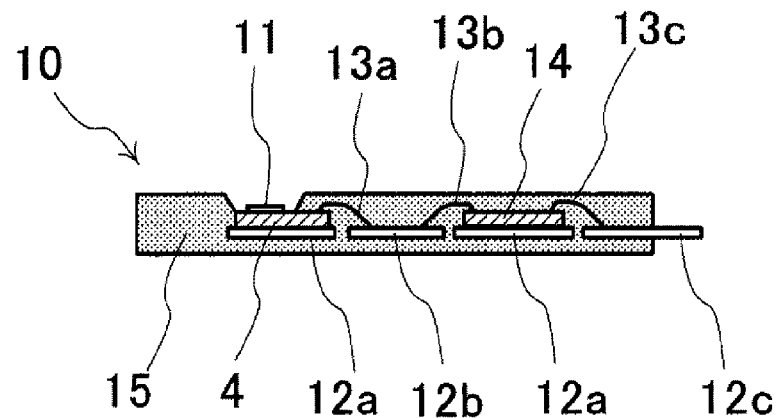

By referring to FIGS. 1 to 4, an embodiment of a gas sensor apparatus and an installation structure of the gas sensor apparatus will be described. FIG. 1 is a cross-sectional view of a gas sensor apparatus and an installation structure of the gas sensor apparatus according to an embodiment of the present invention. FIG. 2 is a cross-sectional view of the gas sensor apparatus of FIG. 1 cut along line II-II. FIGS. 3(a) and 3(b) are enlarged views of a sensor package illustrated in FIG. 2, in which FIG. 3(a) is a plan view and FIG. 3(b) is a cross-sectional view of the internal structure. A gas sensor apparatus 1 is installed to project inward of an air intake passage 2 of an internal combustion engine. In a housing 3 of the gas sensor apparatus 1, a measurement chamber 5 is provided as a first cavity portion in which a humidity sensor element 4, for example, is disposed as a concentration sensor element. The humidity sensor element 4 is a thermal conductive type (thermal) humidity sensor element that uses, for example, a difference in thermal conductivity of air according to humidity of the air. The thermal conductive type (thermal) humidity sensor element measures the concentration based on variations of a resistance value generated from a difference in heat radiation amount radiated into the atmosphere from a heated resistor. A capacitance type humidity sensor element 4 may also be used.

In a housing 3, an expansion chamber 6 is provided as a second cavity portion. The measurement chamber 5 communicates with the expansion chamber 6 by a communicating portion 7. The expansion chamber 6 communicates with the air intake passage 2 via a gas intake port 8. The gas intake port 8 is formed in a bottom portion 3j of the housing 3. The bottom portion 3j of the housing 3 is a side face of the housing 3 arranged approximately in parallel with a gas flow A along the direction of the gas (air) flow A that flows through the air intake passage 2. The intake passage 8 or the gas intake port extends approximately vertically to the direction of the gas flow A toward the expansion chamber 6 from the bottom portion 3j. The communicating passage 7 or the communicating portion extends approximately perpendicularly to both the expansion chamber 6 and the measurement chamber 5 to communicate the expansion chamber 6 with the measurement chamber 5. Both the gas intake port 8 and the communicating portion 7 may have circular or rectangular cross-sections cut along the direction perpendicular to the air flow, or may be in the shape of a slit. The capacity of the gas intake port 8 is preferably larger than that of the communicating portion 7, which will be described in detail later. However, the capacity of the gas intake port 8 is not limited thereto, and may be substantially equal to the capacity of the communicating portion 7.

The gas intake port 8 and the communicating portion 7 each has a capacity smaller than the capacity of the expansion chamber 6 or the measurement chamber 5. When the air flows into the measurement chamber 5 from the gas intake port 8 in this structure, the volume of the air flowing through the air intake passage 2 is squeezed by the gas intake port 8, expanded when the air flows into the expansion chamber 6, squeezed again when the air flows into the communicating portion 7, and expanded again when the air flows into the measurement chamber 5.

The humidity sensor element 4 is stored in a support member, that is, a sensor package 10. The sensor package 10 is a package in which the humidity sensor element 4 is sealed with a sealing resin 15 by an injection molding technique. In the package, a detecting portion 11 of the humidity sensor element 4 is exposed from the sealing resin 15. Accordingly, the humidity sensor element 4 is integrally formed with the sensor package 10 and disposed in the measurement chamber 5 of the housing 3. In this state, the detecting portion 11 of the humidity sensor element 4 is exposed to the measurement chamber 5 to allow measurement of humidity of the air in the measurement chamber 5.

As illustrated in FIG. 2, the housing 3 includes a base 3a and a cover 3b. The sensor package 10, in which the humidity sensor element 4 is stored, is covered by the base 3a and the cover 3b. The base 3a and the cover 3b are molded, adhered, or bonded to form the measurement chamber 5, the expansion chamber 6, the communicating portion 7, and the gas intake port 8.

As illustrated in FIG. 3, lead frames 12a, 12b, and 12c, a semiconductor chip 14, and wires 13a, 13b, and 13c, as well as the humidity sensor element 4, are sealed with the sealing resin 15 to integrally form the sensor package 10. The humidity sensor element 4 is adhered to and fixed on the lead frame 12a. Electrodes (not illustrated) of the humidity sensor element 4 are connected to the lead frame 12b with the wires 13a by wire bonding. A ground electrode of the humidity sensor element 4 is connected to the lead frame 12a with a wire 13a1. The lead frames 12b are electrically connected to input electrodes (not illustrated) of the semiconductor chip 14 via the wires 13b. The lead frames 12c are connected to output electrodes of the semiconductor chip 14 with the wires 13c. A ground electrode of the semiconductor chip 14 is connected to the lead frame 12a with a wire 13c1. The semiconductor chip 14 is a semiconductor integrated chip manufactured according to a semiconductor process, and includes a driving circuit of the humidity sensor element 4 and a detecting circuit for measuring humidity. The semiconductor chip 14 is adhered to and fixed on the lead frame 12a. A power supply line and a detected signal from the semiconductor chip 14 are connected to the lead frames 12c via the wires 13c. The ends of the lead frames 12c are taken out of the sensor package 10 as terminals for external connection. An end 12a1 of the lead frame 12a, which is connected to the ground electrode of the humidity sensor element 4 with the wires 13a1, 13c1, is taken out of the sensor package 10 together with the ends of the lead frames 12c.

In the present embodiment, the lead frame 12a is used as a common ground terminal, and is also used as a member on which the humidity sensor element 4 and the semiconductor chip 14 are mounted. As described above, the humidity sensor element 4, the lead frames 12a to 12c, the semiconductor chip 14, and the wires 13a to 13c are sealed with the sealing resin 15 to form the package. In the package, the detecting portion 11 of the humidity sensor element 4 and the ends of the lead frames 12a, 12c are exposed.

A function and an effect of the gas sensor apparatus 1 of the present embodiment are described. FIGS. 4(*a*) to 4(*c*) are used to explain a function and an effect of the gas sensor apparatus 1 according to the present embodiment, in which FIG. 4(*a*) is related to Embodiment 1, FIG. 4(*b*) is a modification of FIG. 4(*a*), and FIG. 4(*c*) illustrates a past example. In the past example illustrated in FIG. 4 *c*), a gas sensor apparatus 1K has the structure in which the gas intake port 8 is formed to communicate the measurement chamber 5 directly with the air intake passage 2. In the past example, the gas flow A flowing through the air intake passage 2 abuts on a peripheral wall 17 of the passage of the gas intake port 8 and is disturbed. The disturbed air flows into the measurement chamber 5. As a result, the movement of the air increases in the vicinity of the humidity sensor element 4 in the measurement chamber 5, causing an adverse influence on the measurement value of the humidity sensor element 4 and decreasing the measurement accuracy.

In addition, particles P, such as sand or carbon that come flying with the gas flow A, are likely to be disposed on the peripheral wall 17 of the passage of the gas intake port 8. Because of the use in an environment with lots of contaminants or for an extended period of time, the gas intake port 8 may be clogged with the particles P having been disposed on the peripheral wall 17 of the passage of the gas intake port 8, such that good humidity detection is impaired. Water droplets or oil components that come flying with the gas flow A are attached to the housing 3 and turn to droplet Lp. The droplet Lp flows over the outer peripheral side face of the housing 3 by the gas flow A to reach the gas intake port 8. In particular, in a rainy region or a high humidity environment, dew condensation occurs on the housing 3 in addition to the incoming water, and the size of the water droplet becomes bigger. The detection accuracy is, therefore, further decreased.

In the past example, if the capacity of the gas intake port 8 is decreased to restrict the flow-in of the gas flow A into the measurement chamber 5, an anti-contamination characteristic of the gas intake port 8 is decreased. In contrast, if the capacity of the gas intake port 8 is increased to improve the anti-contamination characteristic, the flow-in of the gas flow A into the measurement chamber 5 increases and causes deterioration of the detection accuracy.

FIG. 4(*a*) is an example of the structure of the present embodiment. As described above, the expansion chamber 6 is provided between the measurement chamber 5 and the air intake passage 2. In addition to the expansion chamber 6, a double squeezing structure including the gas intake port 8 and the communicating portion 7 is provided between the air intake passage 2 and the measurement chamber 5. The capacity of the gas intake port 8 is formed larger than that of the communicating portion 7. In the structure according to the embodiment of the present invention, the gas flow A abuts on a stepped portion 17 of the gas intake port 8 and is disturbed. The disturbed gas flow A flows into the expansion chamber 6, causing the movement of the air in the expansion chamber 6, but the influence against the measurement chamber 5 is decreased. In particular, the volume of the gas flow A is squeezed when the gas flow A flows into the gas intake port 8, expanded when the gas flows into the expansion chamber 6, squeezed again when the gas flows into the communicating portion 7, and expanded again when the gas flows into the measurement chamber 5.

The volume of the air flowing into the measurement chamber 5 expands in two stages. By providing the two stages of regions where the volume of the gas expands between the gas intake port 8 and the inside of the expansion chamber 6, the movement of the air in the measurement chamber 5 is decreased. As a result of this, the measuring environment of the humidity sensor element 4 is in a good condition and the measurement accuracy can be improved. In the example structure illustrated in FIG. 4(*a*), the capacity of the gas intake port 8 is increased, such that the clogging of the gas intake port 8 due to the particles P or the droplets Lp can be reduced. Thus, it is possible to maintain the detection accuracy for a long time even in the contaminated or high humidity environment.

Figure 4A:
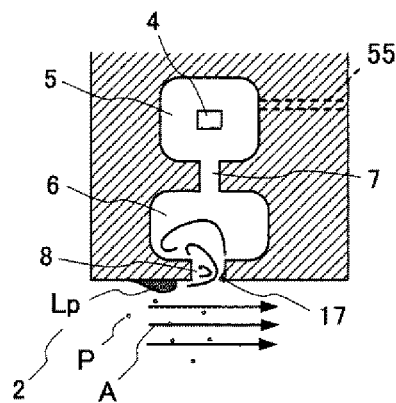

FIG. 4(*b*) illustrates a variation capable of further improving the function and the effect of the present invention. In the variation illustrated in FIG. 4(*b*), a protrusion 19 is provided at the periphery of the gas intake port 8 on the bottom portion 3j located on the side of the air intake passage 2 of the housing 3. The protrusion 19 is provided on the entire periphery surrounding the edge of the opening of the gas intake port 8. The protrusion 19 may be formed integrally with the housing 3, or may be formed separately and fixed to the housing 3 with an adhesive or a fastening member. The protrusion 19 may be provided only on the upstream side of the gas flow A at the periphery of the gas intake port 8. Portions other than those described above are similar to those of FIG. 4(a). Therefore, the same reference signs are given to the corresponding members and the description thereof will not be repeated.

Figure 4B:
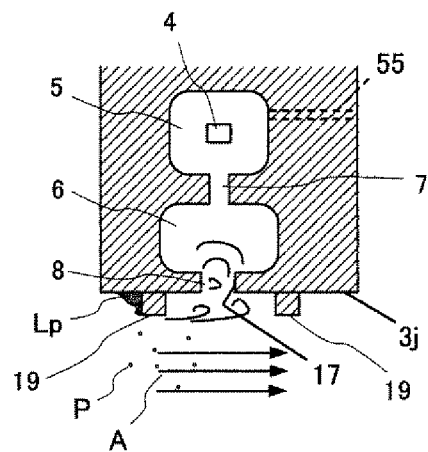

In the structure illustrated in FIG. 4(b), the particles P or the droplets Lp abut on and are trapped by the protrusion 19, which is provided at the periphery of the edge of the opening of the gas intake port 8. It is therefore possible to decrease the adherence of the particles P and the droplets Lp on the peripheral wall 17 of the passage of the gas intake port 8. Thus, it is possible to maintain the detection accuracy for a long time even in the contaminated or high humidity environment.

Figure 4C:
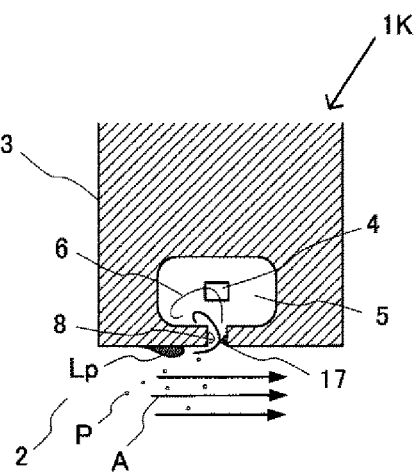

The protrusion 19 may also be formed at the periphery of the edge of the opening of the gas intake port 8 in the past structure illustrated in FIG. 4(c) where only the gas intake port 8 is provided between the air intake passage 2 and the measurement chamber 5. By doing this in the past structure, however, the gas flow A is disturbed by the protrusion 19, and the possibility of occurrence of a swirl increases. The disturbance of air or the generation of the swirl is propagated to the expansion chamber 6. In the past, the internal environment of the measurement chamber 5 changes by such a disturbance of the air or the swirl, and such a change causes noise. In the structure illustrated in FIG. 4(b), the volume of the air flowing into the measurement chamber 5 expands in two stages, as in the structure of FIG. 4(a), such that a good measurement environment of the humidity sensor element 4 can be realized.

Changing the air flowing into the measurement chamber 5 will be described later in another embodiment. A number of gas intake ports 8 may be provided at several positions in the upstream and downstream of the gas flow A. In such a case, the capacity of the gas intake port 8 is obtained as a sum of capacities of all gas intake ports. To guarantee the changing of air flowing into the measurement chamber 5, an outlet 55 that communicates the measurement chamber 5 with the air intake passage 2 may be formed, as indicated by a dotted line in FIGS. 4(a) and 4(b).

According to the present embodiment described above, the following effects are obtained. (1) The double squeezing structure including the gas intake port 8 and the communicating portion 7 are provided, in addition to the expansion chamber 6, between the air intake passage 2 and the measurement chamber 5. The volume of the air expands between the gas intake port 8 and the expansion chamber 6 in two stages of regions. The movement of the air in the measurement chamber 5 is decreased, and the capacity of the gas intake port 8 is made larger than that of the past structure in which only the communicating portion 7 is provided between the air intake passage 2 and the measurement chamber 5. It is possible to reduce clogging of the gas intake port 8 due to the particles P or the droplets Lp contained in the gas flow A, and maintain the detection accuracy for a long time even in the contaminated or high humidity environment.

(2) The movement of the gas in the measurement chamber 5 is suppressed. It is, therefore, possible to prevent the decrease of the detection accuracy even when the thermal humidity sensor element whose detection accuracy is easily affected by the movement of the gas is used.

(3) The gas intake port 8 is formed in the bottom portion 3j of the housing 3. The bottom portion 3j is arranged approximately in parallel with the flowing direction of the gas flow A. The gas flow A flows into the expansion chamber 6 after abutting on the peripheral wall 17 of the passage of the gas intake port 8, and the movement of the air in the expansion chamber 6 is decreased. It is possible to decrease the movement of the air flowing into the measurement chamber 5 from the expansion chamber 6 via the communicating portion 7. (4) The gas intake port 8 is formed in the surface along the air flow of the air intake passage 2 of the housing 3. It is possible to reduce the particles P and the droplets Lp to be attached to the peripheral side face or at the periphery of the edge of the opening of the gas intake port 8.

(5) As illustrated in FIG. 4 (b), the protrusion 19 surrounding the opening of the gas intake port 8 is provided on the bottom portion 3j of the housing 3. With the protrusion 19 provided at the opening of the gas intake port 8, the particles P and the liquid droplets Lp abut on and are trapped by the protrusion 19. It is therefore possible to decrease attachment of the particles P and the droplets Lp on the peripheral wall 17 of the passage of the gas intake port 8.

Embodiment 2

Figure 5:
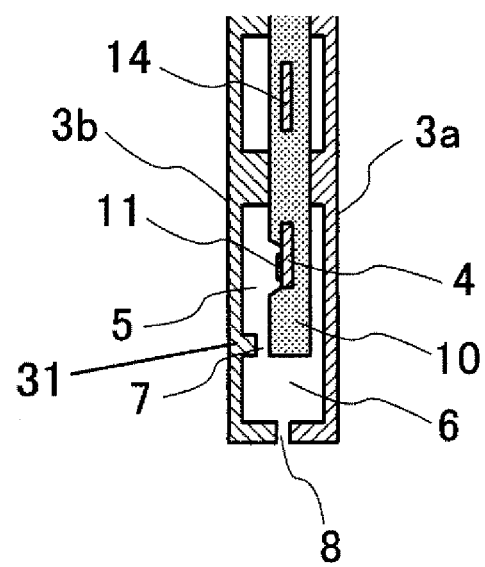
FIG. 5 is a cross-sectional view of the gas sensor apparatus according to Embodiment 2 of the present invention.

FIG. 5 is a cross-sectional view of a gas sensor apparatus according to Embodiment 2 of the present invention. Embodiment 2 of FIG. 5 differs from Embodiment 1 in that the communicating portion 7, which communicates the measurement chamber 5 with the expansion chamber 6, is provided between the sensor package 10 and the cover 3b. In Embodiment 2, a wall portion 31 that projects toward the sensor package 10 is formed at a portion of the cover 3b corresponding to the tip end portion on a side face of the sensor package 10 where the humidity sensor element 4 is provided. The communicating portion 7 is formed between the wall portion 31 of the cover 3b and the side face of the sensor package 10. Portions of Embodiment 2 other than those described above are similar to those of Embodiment 1. Therefore, the same reference signs are given to the corresponding members and the description thereof will not be repeated.

Embodiment 2 can also attain the effect similar to that of Embodiment 1. As is apparent from the comparison with FIG. 2, the housing 3 can be shorter by the length of the communicating portion 7 in the structure of Embodiment 2. This is effective in the gas sensor apparatus for which miniaturization is required. Although a portion of the cover 3b has been projected toward the sensor package 10 in the structure of FIG. 5, it may also be possible to project a portion of the sensor package 10 toward the cover 3b.

Embodiment 3

Figure 6:
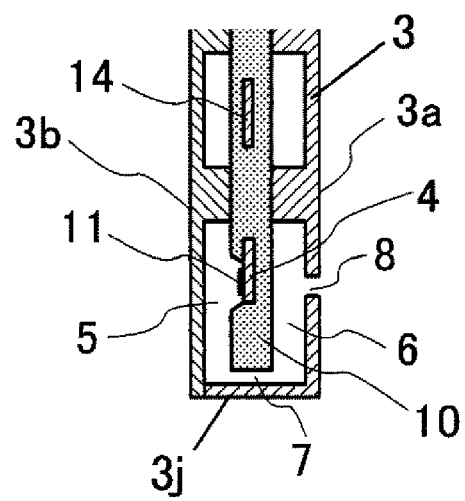
FIG. 6 is a cross-sectional view of a gas sensor apparatus according to Embodiment 3 of the present invention.

FIG. 6 illustrates a gas sensor apparatus according to Embodiment 3 of the present invention. In the structure of Embodiment 3 illustrated in FIG. 6, the expansion chamber 6 is provided between the sensor package 10 and the base 3a, the communicating portion 7 is provided between the tip end portion of the sensor package 10 and the inner face of the bottom portion 3j of the housing 3, and the gas intake port 8 is provided in the side face of the base 3a (the back surface of the housing 3 illustrated in FIG. 1). The expansion chamber 6 is provided opposite to the measurement chamber 5 across the sensor package 10. That is, the expansion chamber 6 is provided to the right of the sensor package 10 nearly opposite to the measurement chamber 5 in FIG. 6. As described above, the communicating portion 7, which communicates the measurement chamber 5 with the expansion chamber 6, is provided between the tip end portion of the sensor package 10 and the housing 3. Accordingly, the length (vertical length in FIG. 1) of the housing 3 can be shorter than that of Embodiments 1 and 2. That is, the length is shorter by the length obtained by subtracting a vertical dimension of the communicating portion 7 in FIG. 6 from a vertical dimension of the expansion chamber 6 in FIG. 1.

As described above, the gas intake port 8 is formed in the right wall of the housing 3 in FIG. 6, that is, in the surface of the housing 3 along the air flow of the air intake passage 2. In this way, the particles P and the droplets Lp attached to the peripheral side face or at the periphery of the end of the opening of the gas intake port 8 are decreased. In addition, the movement of the air in the measurement chamber 5 is decreased.

Portions of Embodiment 3 other than those described above are similar to those of Embodiment 1. Therefore, the same reference signs are given to the corresponding members and the description thereof will not be repeated. Embodiment 3 can also attain the effect similar to that of Embodiment 1. Besides, the gas sensor apparatus of Embodiment 3 can be smaller than the gas sensor apparatus of Embodiment 2. The measurement chamber 5 and the expansion chamber 6 are formed in such a manner that both chambers are substantially and entirely overlapped each other in a planar view of the detecting portion 11 of the humidity sensor element 4. Alternatively, only portions of the both chambers may be overlapped.

Embodiment 4

Figure 7:
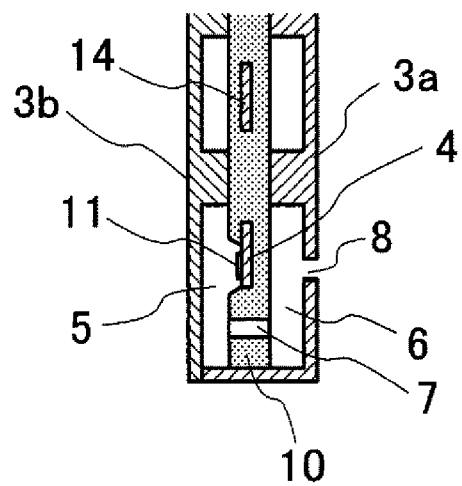
FIG. 7 is a cross-sectional view of the gas sensor apparatus according to Embodiment 4 of the present invention.

FIG. 7 illustrates a gas sensor apparatus according to Embodiment 4 of the present invention. Embodiment 4 illustrated in FIG. 7 differs from Embodiment 3 in that the communicating portion 7 is formed to penetrate through the sensor package 10 in a thickness direction. The communicating portion 7 is formed to penetrate through the sensor package 10 between the humidity sensor element 4, which is provided on the sensor package 10, and the tip end portion of the sensor package 10. The communicating portion 7 thus communicates the measurement chamber 5 provided on a side face of the sensor package 10 with the expansion chamber 6 provided on the opposite side of the sensor package 10.

Portions of Embodiment 4 other than those described above are similar to those of Embodiment 3. Therefore, the same reference signs are given to the corresponding members and the description thereof will not be repeated. Embodiment 4 can also attain the effect similar to that of Embodiment 1. Besides, in the gas sensor apparatus of Embodiment 4, the length of the housing 3 can be decreased by a width (vertical dimension in FIG. 6) of the communicating portion 7 compared to Embodiment 3. Further miniaturization is also possible.

Embodiment 5

FIGS. 8 to 11 illustrate a gas sensor apparatus and an installation structure of the gas sensor apparatus according to Embodiment 5 of the present invention. A complex gas sensor apparatus 20 of Embodiment 5 includes a plurality of sensor elements disposed in the air intake passage 2 of the internal combustion engine. In the following description, the complex gas sensor apparatus 20 includes the humidity sensor 4, a flow rate sensor element 21, and a temperature sensor element 22. These sensor elements are integrally provided. A structure in which the complex gas sensor apparatus 20 is installed in the air intake passage 2 of the internal combustion engine will be described as an example.

Figure 8:
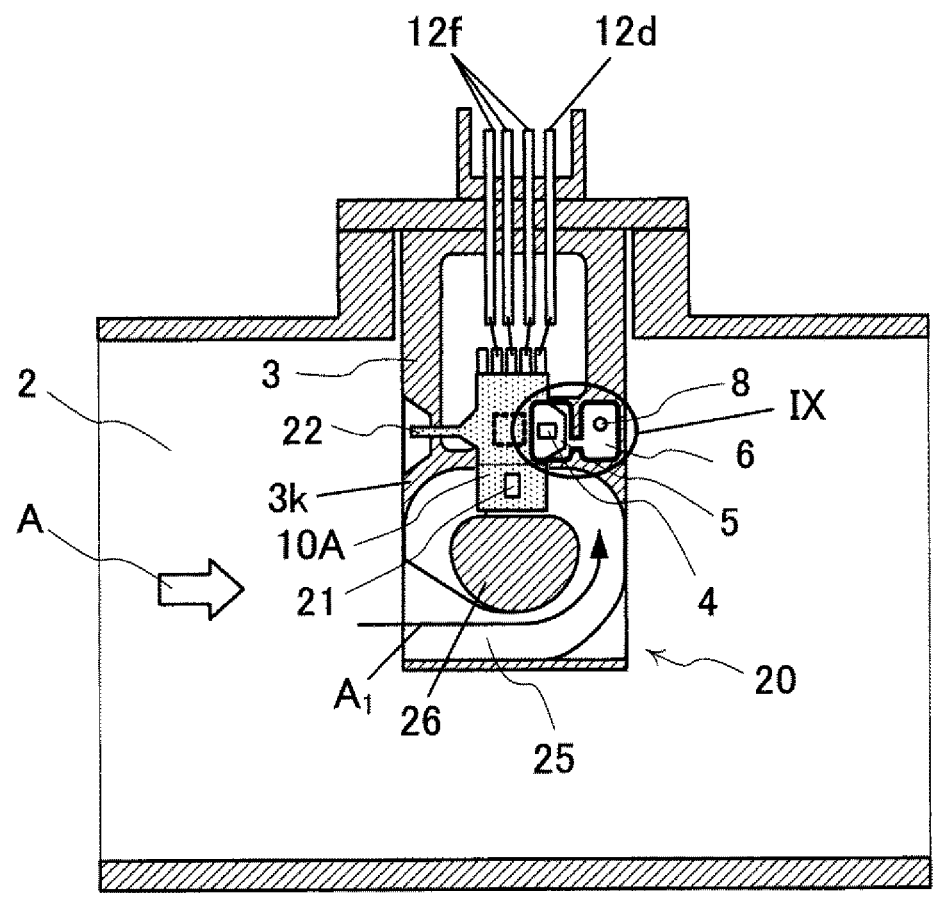
FIG. 8 is a cross-sectional view of a complex gas sensor apparatus and an installation structure of the gas sensor apparatus according to Embodiment 5 of the present invention.
Figure 9:
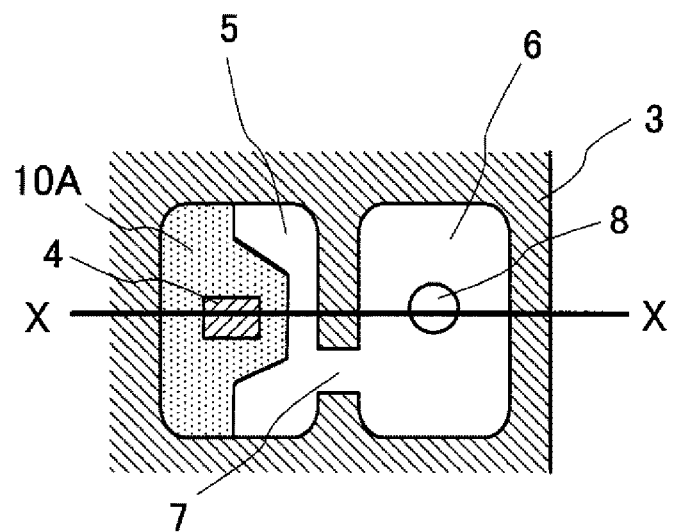
FIG. 9 is an enlarged view of a region IX of FIG. 8.
Figure 10:
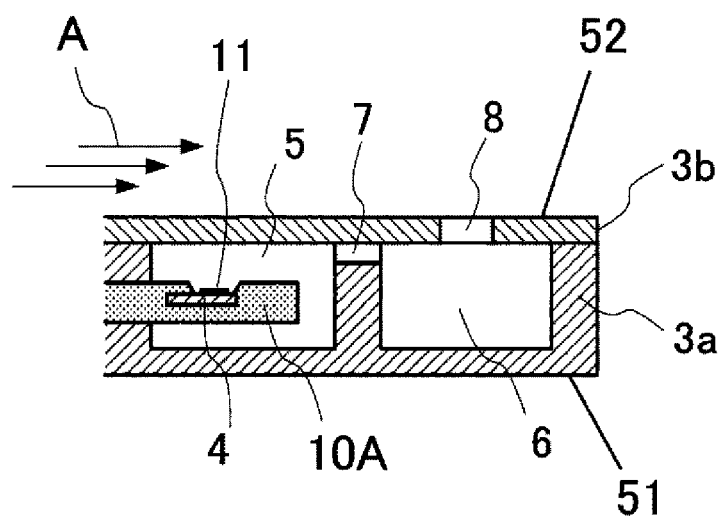
FIG. 10 is a cross-sectional view cut along line X-X of FIG. 9.

FIG. 8 is a cross-sectional view of the complex gas sensor apparatus and the installation structure of the gas sensor apparatus according to Embodiment 5 of the present invention. FIG. 9 is an enlarged view of a region IX of FIG. 8. FIG. 10 is a cross-sectional view cut along line X-X of FIG. 9. In FIG. 8, the complex gas sensor apparatus 20 is installed to project inward in the air intake passage 2 of the internal combustion engine. The humidity sensor element 4, the flow rate sensor element 21, and the temperature sensor element 22 are mounted in the housing 3 of the complex gas sensor apparatus 20. A thermal flow rate sensor element is used as the flow rate sensor element 21 in which a heat generating body is provided at a thin film portion formed in the semiconductor substrate to measure the flow rate according to variations in heat radiation amount or temperature distribution at the periphery of the heat generating body. A thermistor, a temperature measuring resistor, or the like may be used as the temperature sensor element 22. The humidity sensor element 4, the flow rate sensor element 21, and the temperature sensor element 22 are integrated into a sensor package 10A.

A sub-passage 25 that divides the air intake passage 2 is formed in the housing 3. The sub-passage 25 is opened for the gas flow A flowing through the air intake passage 2 of the internal combustion engine. A guide portion 26 that guides a gas flow A1, which has been flowed into the sub-passage 25, toward the flow rate sensor element 21 is formed in the housing 3.

FIGS. 11(*a*) and 11(*b*) are enlarged views of the sensor package 10A illustrated in FIG. 8, in which FIG. 11(*a*) is an external perspective view and FIG. 11 (*b*) is a plan view of the internal structure. The humidity sensor element 4, the flow rate sensor element 21, a detecting portion 11 of the humidity sensor element 4, and a detecting portion 21 of the flow rate sensor element 21 are integrally packaged as the sensor package 10A with the sealing resin 15. The detecting portion 11 of the humidity sensor element 4 and the detecting portion 21 of the flow rate sensor element 21 are exposed. The temperature sensor element 22 is buried in the sealing resin at the tip end portion of a projecting arm portion 10*b* of the sensor package 10A. The semiconductor chip 14 includes a driving circuit that drives the humidity sensor element 4, the flow rate sensor element 21, and the temperature sensor element 22, and a detecting circuit for detection and correction are sealed with the sealing resin 15. The semiconductor chip 14 is sealed with the sealing resin 15 and integrally packaged as the sensor package 10A.

The humidity sensor element 4, the flow rate sensor element 21, and the semiconductor chip 14 are fixed on a lead frame 12*d* with adhesive. The temperature sensor element 22 is disposed at the tip end portion of a lead frame 12*e*. Electrodes (not illustrated) of the humidity sensor element 4 are electrically connected to the semiconductor chip 14 with wires 13*d*. A ground electrode of the humidity sensor element 4 is connected to the lead frame 12*d* with a wire 13*d*1. Similarly, electrodes (not illustrated) of the flow rate sensor element 21 are connected to input electrodes of the semiconductor chip 14 with wires 13*c*. The temperature sensor element 22 is electrically connected to the lead frame 12e and the semiconductor chip 14 by connecting the electrodes of the temperature sensor element 22 with the input electrodes of the semiconductor chip 14 with wires 13e. Lead frames 12f are connected to the output electrodes of the semiconductor chip 14 with wires 13f. A ground electrode of the semiconductor chip 14 is connected to the lead frame 12d with a wire 13f1. End portions of the lead frames 12d, 12f are exposed to the outside from the sensor package 10A.

Figure 11A:
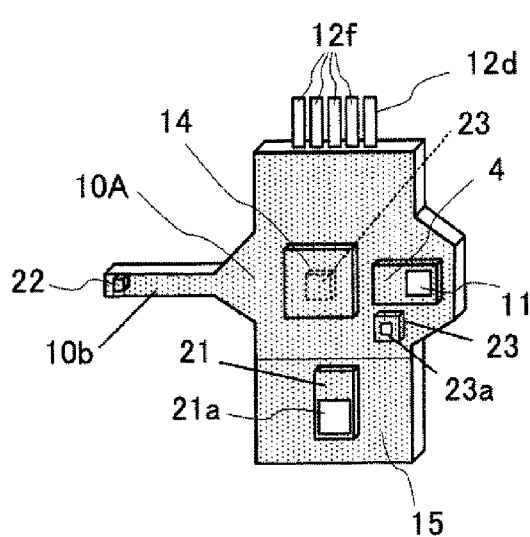
Figure 11B:
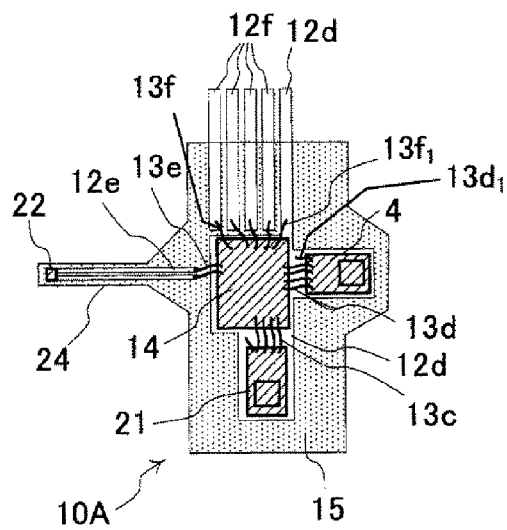

The power supply of the semiconductor chip 14 and a signal detected by the semiconductor chip 14 are respectively connected to the lead frames 12d, 12f via the wires 13f. The electrodes are taken out to the outside of the sensor package 10A. As illustrated in FIG. 11(b), the lead frame 12d is provided as a common ground terminal of the humidity sensor element 4, the flow rate sensor element 21, and the semiconductor chip 14. The lead frame 12d is also used as a member on which the humidity sensor element 4, the flow rate sensor element 21, and the semiconductor chip 14 are mounted.

The sensor package 10A may be formed by the following manufacturing method. (1) The humidity sensor element 4, the flow rate sensor element 21, and the semiconductor chip 14 are fixed by die bonding on the lead frame 12d. (2) The lead frames 12e, 12f are disposed as illustrated in FIGS. 11(a) and 11(b). The electrodes of the humidity sensor element 4, the flow rate sensor element 21, and the temperature sensor element 22 are respectively connected to the electrodes of the semiconductor chip 14 by wire bonding to the wires 13d, 13c, 13e, and 13f, respectively. The lead frame 12d is connected to the ground electrode of the semiconductor chip 14 with the wire 13f1, and the lead frame 12d is also connected to the ground electrode of the humidity sensor 4 with the wire 13d1. The temperature sensor element 22 is mounted on the lead frame 12e, with its electrode (not illustrated) connected to a lead disposed on the lead frame 12e. (3) When the above step (2) is finished, sealing is performed with the sealing resin 15 such that the detecting portions 11, 21a, 23a of the humidity sensor element 4 and the flow rate sensor element 21, respectively, are exposed to the outside, and the end portions of the lead frames 12d, 12f are exposed. The sensor package 10A is thus completed.

By the manufacturing method of the sensor package 10A described above, the sensor elements and the lead frames are sealed with the sealing resin 15. This eliminates the need for fixing fine sensor elements on installation members with adhesive or the like. As a result, the productivity increases and further miniaturization can be realized. By sealing the sensor elements with the sealing resin, the sensor elements can be protected from the external environment physically and chemically, and also protected from electromagnetic noise or solar light.

In the sensor package 10A, as illustrated in FIG. 8, the end portions of the lead frames 12d, 12f are taken out of the housing 3, and the flow rate sensor element 21 is disposed in the sub-passage 25 between a partition wall 3k facing the sub-passage 25 of the housing 3 and the guide portion 26. In the sensor package 10A, the tip end of the arm portion 10b is located in an empty space formed on the outer peripheral wall of the housing 3. In the empty space, the portion where the temperature sensor element 22 is formed is exposed to the gas flow A.

As illustrated in FIGS. 9 and 10, the housing 3 includes the base 3a and the cover 3b. The sensor package 10A, which stores the humidity sensor element 4, is covered by the base 3a and the cover 3b. The base 3a and the cover 3b are molded, adhered, or bonded to form the measurement chamber (first cavity portion) 5, the expansion chamber (second cavity portion) 6, the communicating portion 7, and the gas intake port 8. As illustrated in FIG. 10, a side face (side wall illustrated on the lower side of FIG. 10) 51 of the base 3a and a side face (side wall illustrated on the upper side of FIG. 10) 52 of the cover 3b are arranged in parallel with the gas flow A flowing through the air intake passage 2. The gas intake port 8 is formed in the side face 52 of the cover 3b along the flowing direction of the air intake passage 2. The gas flow A flowing through the air intake passage 2 flows into the expansion chamber 6 through the gas intake port 8 formed in the housing 3.

The measurement chamber 5 and the expansion chamber 6 are divided from each other by the partition wall formed on the base 3a and arranged adjacent to each other. The communicating portion 7, which communicates the measurement chamber 5 with the expansion chamber 6, is provided on the upper side of the partition wall. The humidity sensor element 4 is disposed in the measurement chamber 5 provided in the housing 3. The gas flow A abuts on the peripheral wall 17 of the passage of the gas intake port 8 and is disturbed, and the disturbed air flows into the expansion chamber 6. The air in the expansion chamber 6 is moved, but the influence on the measurement chamber 5 is reduced. In particular, the volume of the gas flow A is squeezed when the gas flow A flows into the gas intake port 8, expanded when the gas flows into the expansion chamber 6, squeezed again when the gas flows into the communicating portion 7, and expanded again when the gas flows into the measurement chamber 5. By providing the two stages of regions where the volume of the air expands between the gas intake port 8 and the inside of the expansion chamber 6, the movement of the air in the measurement chamber 5 is decreased. As a result of this, the measuring environment of the humidity sensor element 4 is in a good condition and the measurement accuracy can be improved.

Since there is substantially no movement of air in the measurement chamber 5, the capacity of the gas intake port 8 can be increased and the clogging of the gas intake port 8 due to the particles P or the droplets Lp can be reduced. It is possible to maintain the detection accuracy for a longtime even in the contaminated or high humidity environment.

Since the complex gas sensor apparatus 20 of Embodiment 5 includes a combination of the humidity sensor element 4, the flow rate sensor element 21, and the temperature sensor element 22, it is possible to provide a digital correcting function in the semiconductor chip 14 to correct signals from individual sensor elements to improve accuracy.

The measurement chamber 5 and the expansion chamber 6 are arranged adjacent to each other in a planar view in Embodiment 5, but a different arrangement may also be possible. In the following, the complex gas sensor apparatus having a different structure will be described.

Embodiment 6

Figure 12:
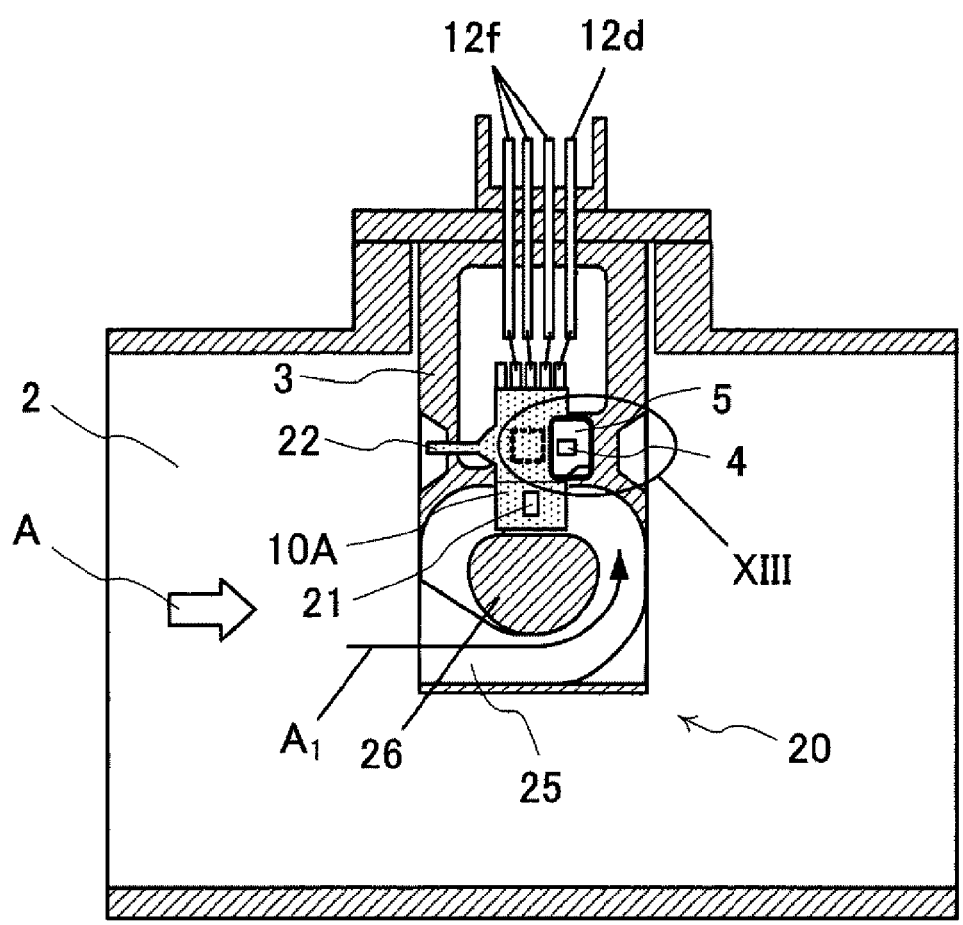
FIG. 12 is a cross-sectional view of a gas sensor apparatus and an installation structure of the gas sensor apparatus according to Embodiment 6 of the present invention.
Figure 13:
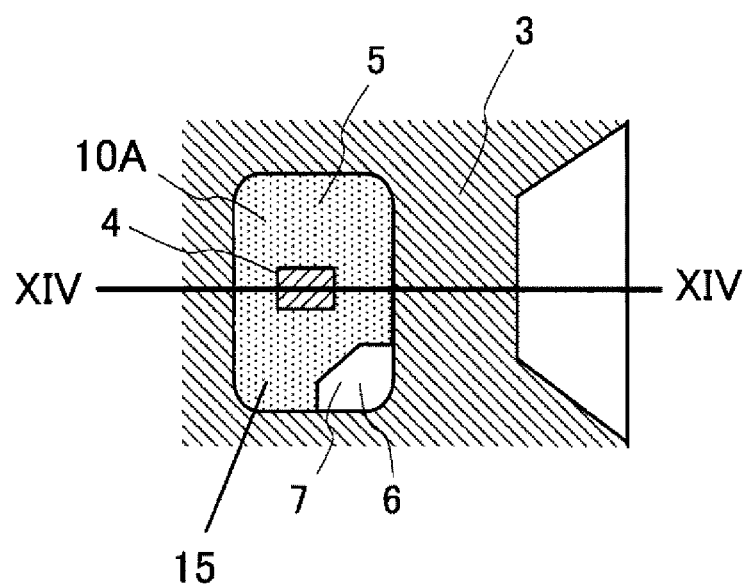
FIG. 13 is an enlarged view of a region XIII of FIG. 12.
Figure 14:
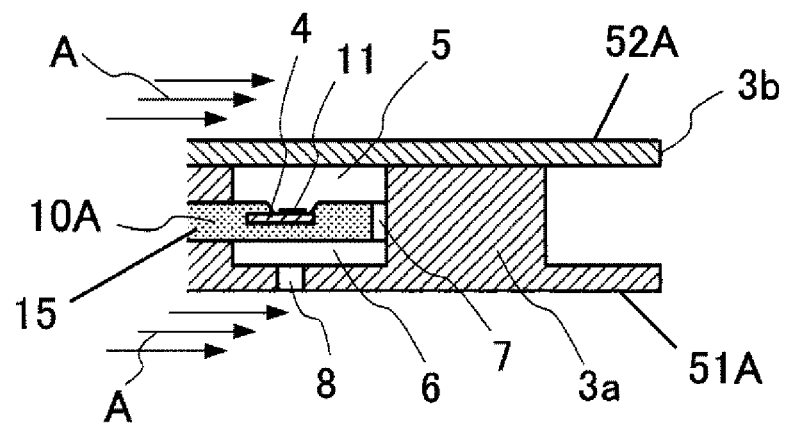
FIG. 14 is a cross-sectional view cut along line XIV-XIV of FIG. 13.

FIGS. 12 to 14 illustrate a gas sensor apparatus and an installation structure of the gas sensor apparatus according to Embodiment 6 of the present invention, in which FIG. 12 is a cross-sectional view, FIG. 13 is an enlarged view of a region XIII of FIG. 12, and FIG. 14 is a cross-sectional view cut along line XIV-XIV of FIG. 13. A complex gas sensor apparatus 20 of Embodiment 6 differs from that of Embodiment 5 in the arrangement of the measurement chamber 5 and the expansion chamber 6 and in the structure of the communicating portion 7 communicating the measurement chamber 5 with the expansion chamber 6.

In the complex gas sensor apparatus 20 illustrated in Embodiment 6, the expansion chamber 6 is disposed opposite to the measurement chamber 5 in the sensor package 10A, as illustrated in FIG. 14, in such a manner that the expansion chamber 6 substantially entirely overlaps the measurement chambers. The communicating portion 7, which communicates the measurement chamber 5 with the expansion chamber 6, is provided between the tip end of the sensor package 10A and the inner side walls of the housing 3. A length (lateral distance in FIG. 12) of the housing 3 is decreased compared to that of Embodiments 1 and 2. That is, the length is decreased by a distance obtained by subtracting a vertical dimension of the communicating portion 7 in FIG. 1 from a vertical dimension of the expansion chamber 6 in FIG. 14.

The housing 3 includes the base 3a and the cover 3b. The sensor package 10A, which stores the humidity sensor element 4, is covered by the base 3a and the cover 3b. The base 3a and the cover 3b are molded, adhered, or bonded to form the measurement chamber 5, the expansion chamber 6, the communicating portion 7, and the gas intake port 8. A side face 51A of the base 3a and a side face 52A of the cover 3b are arranged in parallel with the gas flow A flowing through the air intake passage 2. The gas intake port 8 is provided on the side face 51A of the base 3a along the flowing direction of the air intake passage 2. The gas flow A flowing through the air intake passage 2 flows into the expansion chamber 6 through the gas intake port 8 formed in the housing 3. Portions of Embodiment 6 other than those described above are similar to those of Embodiment 5. Therefore, the same reference signs are given to the corresponding members and the description thereof will not be repeated.

In the complex gas sensor apparatus 20 of Embodiment 6, two stages of regions where the volume of the air expands are also provided between the gas intake port 8 and the inside of the expansion chamber 6, the movement of the air in the measurement chamber 5 can be decreased. The capacity of the gas intake port 8 is increased, such that the clogging of the gas intake port 8 due to the particles P or the droplets Lp can be reduced. The effect similar to that of the complex gas sensor apparatus 20 of Embodiment 5 is obtained.

In the complex gas sensor apparatus 20 of Embodiment 6, the expansion chamber 6 is provided on the side of the sensor package 10A opposite to the side where the humidity sensor element 4 is provided. The amount of air that flows in contact with the sensor package 10A is larger than that of the complex gas sensor apparatus 20 of Embodiment 5. This facilitates cooling of the sensor package 10A. The semiconductor chip 14 and the humidity sensor element 4, both generating heat by themselves, are cooled via the expansion chamber 6 to suppress the variations in temperature, such that the humidity sensor element 4 can measure humidity in a stable environment.

Embodiment 7

Figure 15:
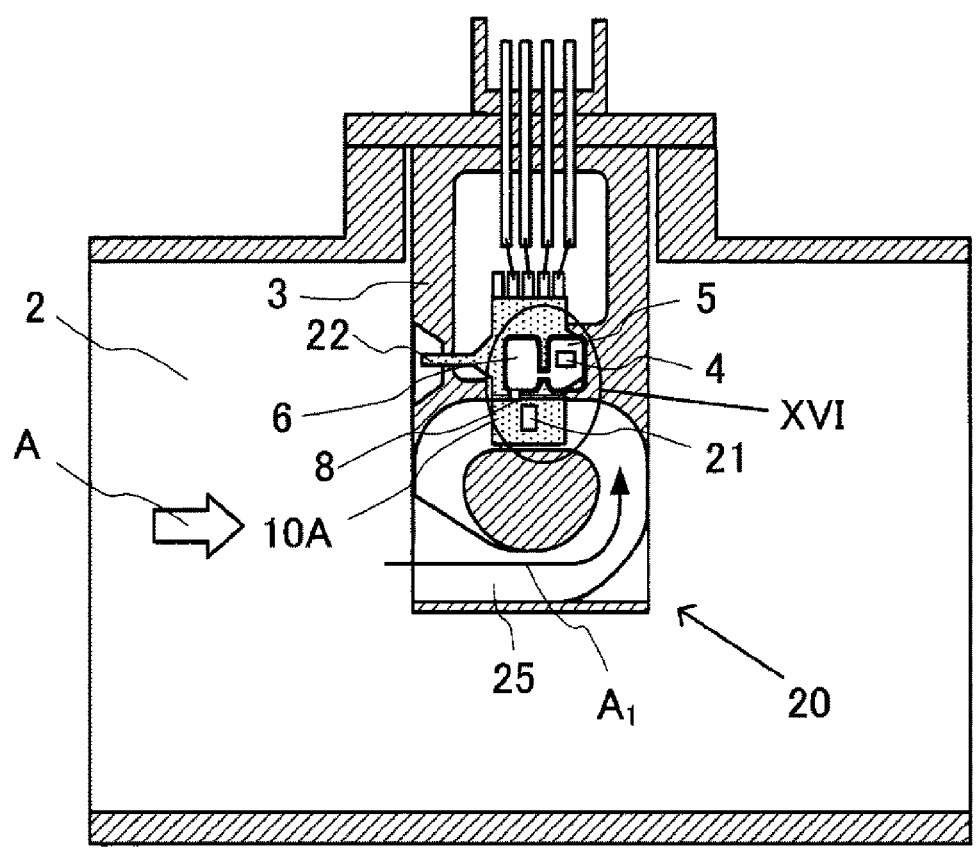
FIG. 15 is a cross-sectional view of a gas sensor apparatus according to Embodiment 7 of the present invention.
Figure 16:
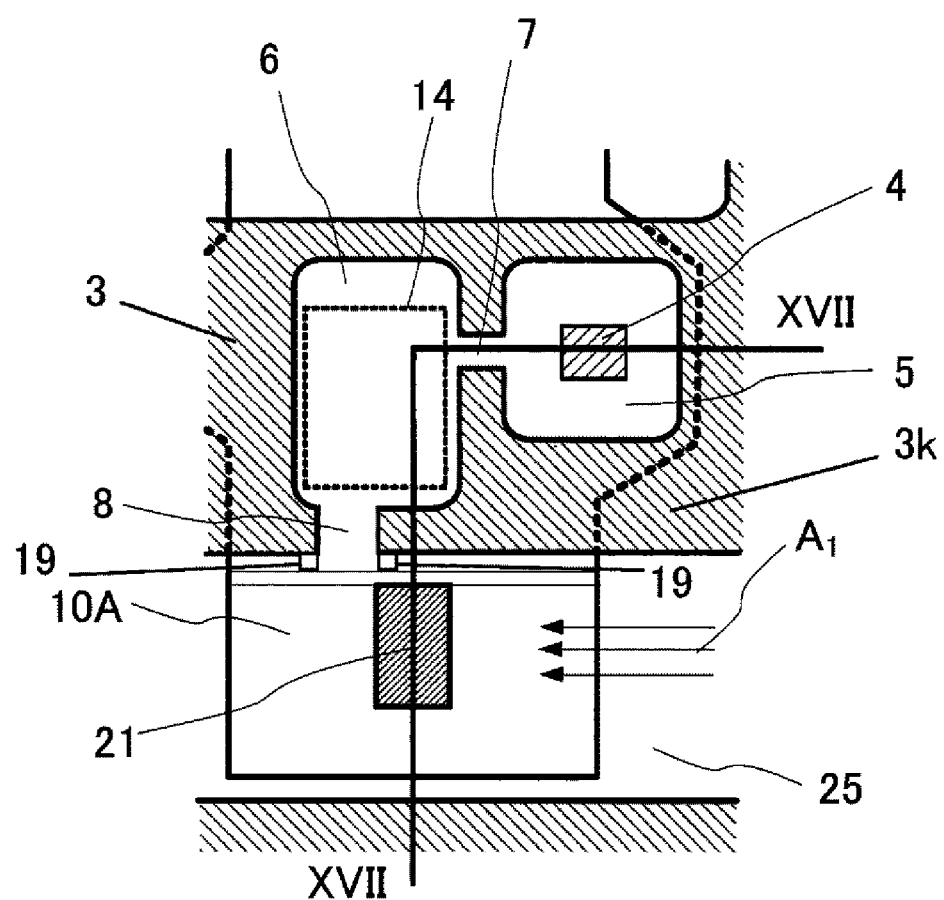
FIG. 16 is an enlarged view of a region XVI of FIG. 15.
Figure 17:
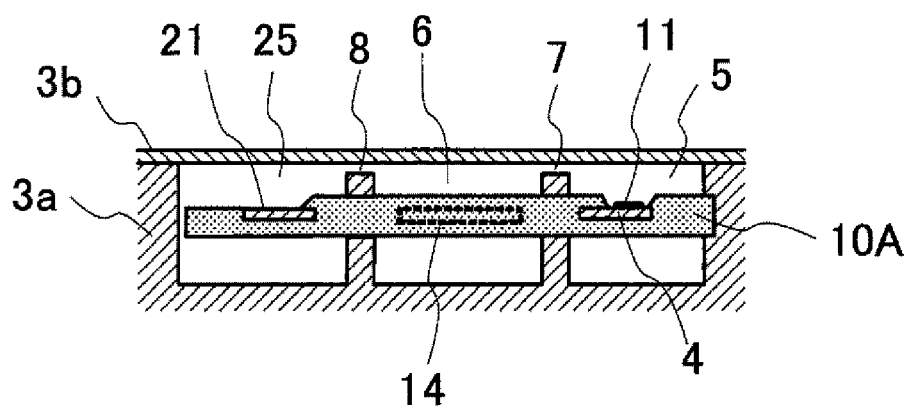
FIG. 17 is a cross-sectional view cut along line XVII-XVII of FIG. 16.

FIGS. 15 to 17 illustrate a gas sensor apparatus and an installation structure of the gas sensor apparatus according to Embodiment 7 of the present invention, in which FIG. 15 is a cross-sectional view of the gas sensor apparatus, FIG. 16 is an enlarged view of a region XVI of FIG. 15, and FIG. 17 is a cross-sectional view cut along line XVII-XVII of FIG. 16. A complex gas sensor apparatus 20 of Embodiment 7 differs from that of Embodiment 5 in the arrangement and the structure of the expansion chamber 6, the measurement chamber 5, and the gas intake port 8. The expansion chamber 6 and the measurement chamber 5 are divided by a side wall of the housing 3 and arranged adjacent to each other in a direction along the gas flow A. The communicating portion 7 is formed by opening a part of the side wall between the expansion chamber 6 and the measurement chamber 5 to communicate the expansion chamber 6 with the measurement chamber 5. The gas intake port 8 is formed by opening the side wall of the sub-passage 25 of the expansion chamber 6 to communicate the expansion chamber 6 with the sub-passage 25.

The protrusion 19 is provided at the periphery of the gas intake port 8 protruding toward the sub-passage 25 from the partition wall 3k of the housing 3. The partition wall 3k divides the expansion chamber 6 from the sub-passage 25. The protrusion 19 may be formed integrally with the housing 3, or may be formed separately and bonded to the housing 3. As illustrated in FIG. 17, the semiconductor chip 14 stored in the sensor package 10A is disposed in the expansion chamber 6. Portions of Embodiment 7 other than those described above are similar to those of Embodiment 5, such that the same reference signs are given to the corresponding members and the description thereof will not be repeated.

In the complex gas sensor apparatus 20 of Embodiment 6, two stages of regions where the volume of the air expands are also provided between the gas intake port 8 and the inside of the expansion chamber 6, the movement of the air in the measurement chamber 5 can be decreased. The capacity of the gas intake port 8 is increased, such that the clogging of the gas intake port 8 due to the particles P or the droplets Lp can be reduced. The effect similar to that of the complex gas sensor apparatus 20 of Embodiment 5 is obtained.

In the complex gas sensor apparatus 20 of Embodiment 7, the protrusion 19 is formed at the periphery of the gas intake port 8. The particles P and the liquid droplets Lp contained in the gas flow A1 flowing through the sub-passage 25 abut on and are trapped by the protrusion 19. It is therefore possible to decrease the attachment of the particles P and the droplets Lp on the peripheral wall 17 of the passage of the gas intake port 8. Thus, it is possible to maintain the detection accuracy for a long time even in the contaminated or high humidity environment.

In the gas sensor apparatus 20 of Embodiment 7, the semiconductor chip 14 stored in the sensor package 10A is disposed in the expansion chamber 6. There is a space around the semiconductor chip 14 to form the expansion chamber 6. Even when the housing 3 is subjected to expansion/contraction due to heating, the stress transmitted to the semiconductor chip 14 can be reduced. It is therefore possible to suppress the variations of the circuit characteristic of the semiconductor chip 14 generated in association with the stress. It is also possible to attain a cooling effect of the semiconductor chip 14 by the air flowing in the expansion chamber 6.

Embodiment 8

Figure 18:
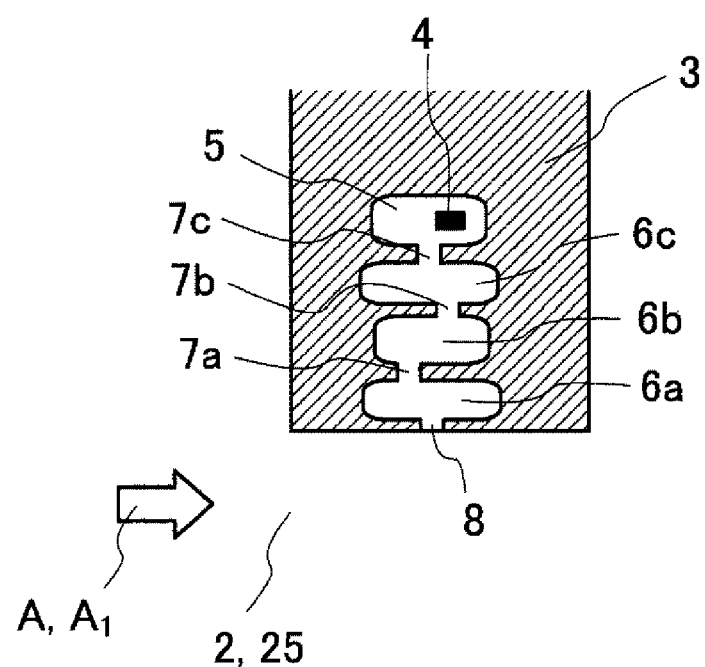
FIG. 18 is a schematic plan view illustrating the arrangement of an expansion chamber and a measurement chamber according to Embodiment 8 of the present invention.

FIG. 18 is a schematic plan view of an arrangement of the expansion chamber 6 and the measurement chamber 5 formed in the housing 3 according to Embodiment 8 of the present invention. The sensor package 10 is not illustrated in FIG. 18. In FIG. 18, the expansion chamber 6 includes a plurality of expansion chambers (three chambers are illustrated in FIG. 18). The expansion chamber 6 includes a first expansion chamber 6a, a second expansion chamber 6b, and a third expansion chamber 6c formed adjacent to each other in this order from the side facing the gas flow A toward the measurement chamber 5, and divided by the partition wall of the housing 3. The first expansion chamber 6a communicates with the air intake passage 2 and the passage 25 where the gas flow A, A1 flows through the gas intake port 8 formed by opening the partition wall of the housing 3. The first expansion chamber 6a and the second expansion chamber 6b communicate each other via a first communicating portion 7a formed by opening the partition wall of the housing 3. The second expansion chamber 6b and the third expansion chamber 6c communicate with each other via a second communicating portion 7b formed by opening the partition wall of the housing 3. The third expansion chamber 6c communicates with the measurement chamber 5 via a third communicating portion 7c formed by opening the partition wall of the housing 3. The humidity sensor element 4 is disposed in the measurement chamber 5.

Embodiment 8 includes three expansion chambers 6a to 6c and three communicating portions 7a to 7c. The volume of the gas flow A, A1 flowing into the measurement chamber 5 from the air intake passage 2 or the sub-passage 25 expands in four stages. The movement of the air in the expansion chamber 6 decreases as the gas flow A, A1 expands. Accordingly, the movement of air in the measurement chamber 5 becomes very small. The capacity of the gas intake port 8 is increased, such that the clogging of the gas intake port 8 due to the particles P or the droplets Lp can be reduced. It is possible to maintain the detection accuracy for a long time even in the contaminated or high humidity environment.

The structure of Embodiment 8 described above, in which the plurality of expansion chambers 6 are provided to communicate with each other, can be used in the gas sensor apparatuses 1, 20 of Embodiments 1, 2, 5, and 7. The gas sensor apparatuses 1, 20 of Embodiments 3, 4, and 6, in which the expansion chamber 6 is arranged to overlap the measurement chamber 5 in a planar view, may also include the plurality of expansion chambers 6 provided to communicate with each other in a planar view by the communicating portion 7. Alternatively, the expansion chambers 6 may be formed in a plurality of layers and arranged vertically to overlap on top of each other in a planar view. The layers of the expansion chambers 6 may be communicated with each other by the communicating portion 7.

Embodiment 9

Figure 19:
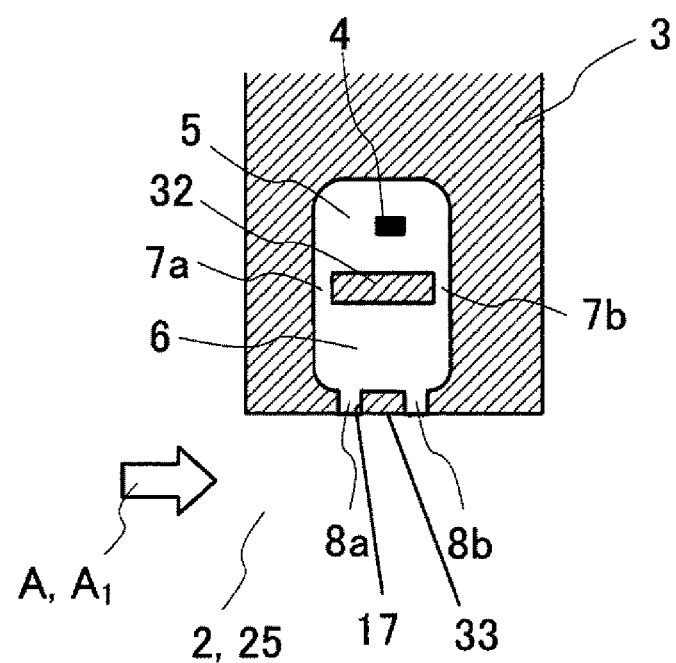
FIG. 19 is a schematic plan view illustrating the structure of an expansion chamber and a measurement chamber according to Embodiment 9 of the present invention.

FIG. 19 is a schematic plan view of the structure of the expansion chamber 6 and the measurement chamber 5 formed in the housing 3 according to Embodiment 9 of the present invention. The sensor package 10 is not illustrated in FIG. 19. The measurement chamber 5 and the expansion chamber 6 of the gas sensor apparatus of FIG. 19 are formed by dividing an approximately rectangular space, which is formed by the base 3a and the cover 3b constituting the housing 3, into two parts by a partition wall 32. The partition wall 32 may be formed integrally with the base 3a or the cover 3b, or may be provided as a separate member and fixed to the base 3a or the cover 3b with adhesive, by fastening, or the like. A first communicating portion 7a is formed between one longitudinal end of the partition wall 32 and a side face of the housing 3. A second communicating portion 7b is formed between the other longitudinal end of the partition wall 32 and another side face of the housing 3.

The largest feature of Embodiment 9 is that more than one gas intake port 8a, 8b (two ports are illustrated in FIG. 19), which communicates the air intake passage 2 or the sub-passage 25 with the expansion chamber 6, is provided on both end portions of a partition 33 along the flow direction of the gas flow A, A1. With the plurality of gas intake ports 8a, 8b provided along the flow direction of the gas flow A, A1, a pressure difference is generated between the gas intake ports 8a, 8b, because a larger pressure is applied in the upstream side than in the downstream side of the gas flow. Accordingly, the air flows into the expansion chamber 6 from the gas intake port 8a, and the air in the expansion chamber 6 is exhausted from the gas intake port 8b. This indicates that a small movement of air occurs in the expansion chamber 6.

Embodiment 9 also includes the two stages of regions where the volume of the gas expands in the expansion chamber 6 from the gas intake port 8, such that the movement of the air in the measurement chamber 5 can be reduced. The capacity of the gas intake port 8 is increased, such that the clogging of the gas intake port 8 due to the particles P or the droplets Lp can be reduced. The effect similar to that of the gas sensor apparatuses 1, 20 of Embodiments 1 to 7 is obtained.

The plurality of gas intake ports 8a, 8b are provided in Embodiment 9. In the case where the internal combustion engine is used under adverse environmental conditions, lots of droplets Lp may be generated and the gas intake port 8a may be clogged by capillary phenomenon. With the plurality of gas intake ports 8a, 8b, however, it is possible to prevent complete clogging of the gas intake ports 8a, 8b. In addition, since the gas intake ports 8a, 8b are arranged in the direction along the gas flow A, A1, a small movement of air is generated such that the air flows into the expansion chamber 6 from the gas intake port 8a and is exhausted from the expansion chamber 6 via the gas intake port 8b. Therefore, the effect of discharging the particles P or the droplets Lp, which come through the gas intake port 8a, from the gas intake port 8b is obtained. That is, the clogging of the gas intake port 8a with the droplets Lp attached to the peripheral wall 17 of the passage is recovered by self-cleaning activity. In Embodiment 9, the two communicating portions 7a, 7b may be combined to one portion.

Embodiment 10

Figure 20:
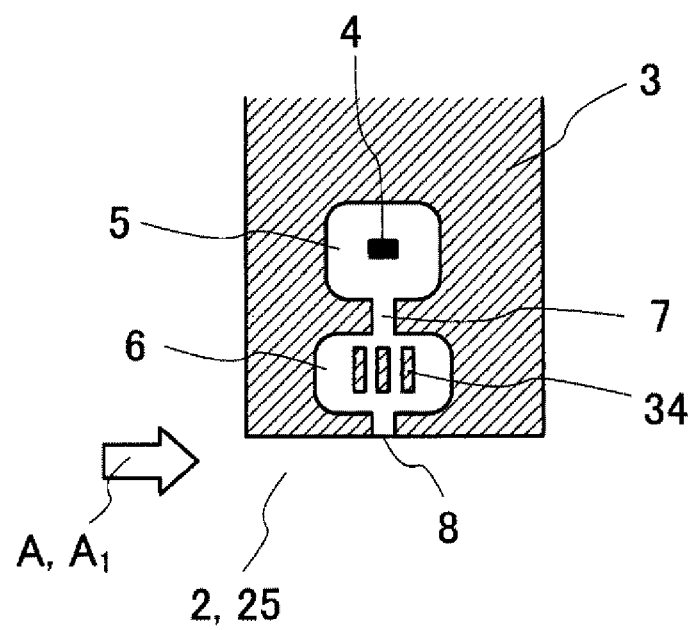
FIG. 20 is a schematic plan view of the structure of an expansion chamber and a measurement chamber according to Embodiment 10 of the present invention.

FIG. 20 is a schematic plan view of the structure of the expansion chamber 6 and the measurement chamber 5 formed in the housing 3 according to Embodiment 10 of the present invention. The sensor package 10 is not illustrated in FIG. 20. Similar to the gas sensor apparatus 1 of Embodiment 1 (see FIG. 1), the expansion chamber 6 and the measurement chamber 5 of the gas sensor apparatus of Embodiment 10 are divided by a partition wall and arranged adjacent to each other in the housing 3. The measurement chamber 5 and the expansion chamber 6 communicate with each other by the communicating portion 7. The expansion chamber 6 communicates with the air intake passage 2 or the sub-passage 25 via the gas intake port 8.

The largest feature of Embodiment 10 is that more than one protrusion (trap) 34 is formed in the expansion chamber 6. The protrusions 34 may be formed integrally with the base 3a or the cover 3b constituting the housing 3, or may be provided as a separate member and fixed to the base 3a or the cover 3b with adhesive, by fastening, or the like. The protrusions 34 are formed in the shape of plates or columns and arranged at the periphery of a region including a straight line connecting the communicating portion 7 and the gas intake port 8.

In the internal combustion engine, when the internal combustion engine stops, oil in the combustion chamber or a supercharger may immediately be vaporized and diffused in the air intake passage 2, and come flying to the gas sensor apparatus 1, 20. The vapor of the oil enters through a gap in the gas sensor apparatus 1, 20 into the measurement chamber 5. The protrusions 34 have a function to trap such vapor of the oil.

In the gas sensor apparatus 1, 20 of Embodiment 10, the two stages of regions where the volume of the air expands are also provided between the gas intake port 8 and the inside of the expansion chamber 6. Therefore, the movement of the air in the measurement chamber 5 can be reduced. The capacity of the gas intake port 8 is increased, such that the clogging of the gas intake port 8 due to the particles P or the droplets Lp can be reduced. The effect similar to that of the gas sensor apparatuses 1, 20 of Embodiments 1 to 9 is obtained.

The protrusions 34 are formed in the expansion chamber 6 to trap the vapor of the oil in Embodiment 10. When the gas sensor apparatus 1, 20 of the above embodiments is used in the internal combustion engine to measure the concentration of the components contained in the gas flow A flowing through the air intake passage 2, the vapor of the oil that come flying through the air intake passage 2 is trapped. Therefore, it is possible to maintain the measurement accuracy of the concentration sensor element disposed in the measurement chamber 5 for a long time.

In the structure of the above embodiments, the humidity sensor element 4 is provided in the measurement chamber 5. Alternatively, other concentration sensor elements, such as a hydrogen sensor element, an oxygen sensor element, or a $CO_2$ sensor element, may be used, instead of the humidity sensor element 4. A number of types of the concentration sensor elements may be arranged in the measurement chamber 5. The concentration sensor, such as a humidity sensor element, or particularly a thermal transmission type (thermal) concentration sensor element that uses a difference in thermal conductivity of gas according to the concentration of the gas and measures the concentration based on variations of a resistance value, is largely affected, compared to the temperature sensor, by the measurement accuracy caused by the movement of air. The gas sensor apparatuses 1, 20 of the above embodiments can attain a larger effect in terms of maintaining the measurement accuracy for the thermal concentration sensor element. As to the clogging of the gas intake port 8 due to the particles P or the droplets Lp, since the capacity of the gas intake port 8 is increased, the effect can be expected for both the capacitance type and thermal type concentration sensors in terms of maintaining the detection accuracy for a long time.

In addition to the concentration sensor element, the complex gas sensor apparatus 20 has been illustrated as including the flow rate sensor element 21 and the temperature sensor element 22. However, the complex gas sensor apparatus 20 may exclude one or more sensor element or include another environmental sensor element.

The sensor packages 10, 10A of the above embodiments have been illustrated as having the packaged structure by sealing the humidity sensor element 4, the flow rate sensor element 21, and the temperature sensor element 22 with the sealing resin 15. However, the structure of the sensor packages 10, 10A may not be limited to packaging the sensor elements with the sealing resin 15, and may also have the structure in which some or all sensor elements are fixed to the supporting member with adhesive, by fastening, or the like.

The gas sensor apparatuses 1, 20 of the present invention may be used in the internal combustion engine other than the internal combustion engine for vehicles, and also be used to measure the gas concentration in various environments.

The above embodiments have been illustrated as examples only, and Embodiments 1 to 10 may be appropriately combined or changed according to the spirit of the invention. In short, any gas sensor apparatus may be used so long as it includes the housing including a first cavity portion that stores the concentration sensor element, a second cavity portion disposed between the first cavity portion and the gas intake port, and a communicating portion that communicates the first cavity portion with the second cavity portion.

REFERENCE SIGNS LIST 1, 20 gas sensor apparatus
2 air intake passage
3 housing
3a base
3b cover
4 humidity sensor element
5 measurement chamber (first cavity portion)
6 expansion chamber (second cavity portion)
7 communicating portion
8 gas intake port
10, 10A sensor package
15 sealing resin
21 flow rate sensor element
22 temperature sensor element
25 sub-passage
34 protrusion (trap)
A, $A_1$ air flow (gas flow)
$L_p$ droplet
P particle

The invention claimed is:

1. A gas sensor apparatus, comprising:
a concentration sensor element configured to detect concentration of a predetermined component in a fluid that is subject to detection;
a supporting member configured to support the concentration sensor element in such a manner that the concentration sensor element is exposed in a passage through which the fluid subject to detection flows; and
a housing, the housing including
the concentration sensor element having a detecting portion and fixed to the supporting member,
a first cavity portion at least covering a region of the supporting member where the concentration sensor element is fixed, and storing the concentration sensor element with the detecting portion being exposed,
a gas intake port that is opened externally,
a second cavity portion provided between the first cavity portion and the gas intake port,
a communicating portion communicating the first cavity portion with the second cavity portion, wherein
the communicating portion and the gas intake port each has a capacity smaller than a capacity of the second cavity portion,
the housing includes a base and a cover that covers the base, the base having a partition wall that divides the first cavity portion and the second cavity,
the gas intake port is formed in the cover, the communicating portion is formed to penetrate through the partition wall, and
a protrusion is provided at the periphery of the gas intake port.

2. The gas sensor apparatus according to claim 1, wherein the first cavity portion and the second cavity portion are arranged at a position where the first cavity portion and the second cavity portion are at least partially overlapped in a planar view.

3. The gas sensor apparatus according to claim 2, wherein the communicating portion is formed to penetrate through the supporting member in a thickness direction.

4. The gas sensor apparatus according to claim 1, wherein a trap is formed in the second cavity portion to trap the gas.

5. The gas sensor apparatus according to claim 1, further comprising:
an environmental sensor element configured to measure an environmental element other than the environmental element measured by the concentration sensor element, wherein
the concentration sensor element and the environmental sensor element are packaged with a sealing resin together with the supporting member.

6. The gas sensor apparatus according to claim 5, wherein the concentration sensor element is a humidity sensor element, and the environmental sensor element includes a plurality of sensor elements including a temperature sensor element and a flow rate sensor element.

7. The gas sensor apparatus according to claim 6, wherein the supporting member is a lead frame, and
the concentration sensor element and the environmental sensor elements are mounted on the lead frame, connected to lead terminals by wire bonding, and connected to the lead frame by wire bonding.

8. An installation structure of a gas sensor apparatus, comprising:
the gas sensor apparatus according to claim 1; and
an internal combustion engine in which the gas sensor apparatus is installed in an air intake passage, wherein
the gas intake port of the gas sensor apparatus is formed in a side face of the housing approximately in parallel with the direction of the air flow flowing through the air intake passage, or in a side face on a rear side of the housing relative to the gas flowing through the air intake passage.

9. The installation structure of the gas sensor apparatus according to claim 8, wherein
the protrusion is formed in the upstream side of the gas flowing through the air intake passage.

10. The installation structure of the gas sensor apparatus according to claim 8, wherein
the plurality of gas intake ports are provided on the side face of the housing along the direction of the gas flowing through the air intake passage.

11. The installation structure of the gas sensor apparatus according to claim 8, wherein
the gas sensor apparatus at least includes a humidity sensor element and a flow rate sensor element,
the housing includes a sub-passage through which part of the gas flowing through the air intake path is taken,
the humidity sensor element is stored in the first cavity portion, and
the flow rate sensor element is arranged in the sub-passage.

12. An installation structure of a gas sensor apparatus, comprising:
a gas sensor apparatus; the gas sensor comprising:
a concentration sensor element configured to detect concentration of a predetermined component in a fluid that is subject to detection;
a supporting member configured to support the concentration sensor element in such a manner that the concentration sensor element is exposed in a passage through which the fluid subject to detection flows; and
a housing, the housing including
the concentration sensor element having a detecting portion and fixed to the supporting member,
a first cavity portion at least covering a region of the supporting member where the concentration sensor element is fixed, and storing the concentration sensor element with the detecting portion being exposed,
a gas intake port that is opened externally,
a second cavity portion provided between the first cavity portion and the gas intake port,
a communicating portion communicating the first cavity portion with the second cavity portion, wherein
the communicating portion and the gas intake port each has a capacity smaller than a capacity of the second cavity portion; and
an internal combustion engine in which the gas sensor apparatus is installed in an air intake passage, wherein
the gas intake port of the gas sensor apparatus is formed in a side face of the housing approximately in parallel with the direction of the air flow flowing through the air intake passage, or in a side face on a rear side of the housing relative to the gas flowing through the air intake passage, and
at least one protrusion is formed at the gas intake port of the housing in the upstream side of the gas flowing through the air intake passage.

13. An installation structure of a gas sensor apparatus, comprising:
a gas sensor apparatus; the gas sensor comprising:
a concentration sensor element configured to detect concentration of a predetermined component in a fluid that is subject to detection;
a supporting member configured to support the concentration sensor element in such a manner that the concentration sensor element is exposed in a passage through which the fluid subject to detection flows; and
a housing, the housing including
the concentration sensor element having a detecting portion and fixed to the supporting member,
a first cavity portion at least covering a region of the supporting member where the concentration sensor element is fixed, and storing the concentration sensor element with the detecting portion being exposed,
a gas intake port that is opened externally,
a second cavity portion provided between the first cavity portion and the gas intake port,
a communicating portion communicating the first cavity portion with the second cavity portion, wherein
the communicating portion and the gas intake port each has a capacity smaller than a capacity of the second cavity portion; and an internal combustion engine in which the gas sensor apparatus is installed in an air intake passage, wherein the gas intake port of the gas sensor apparatus is formed in a side face of the housing approximately in parallel with the direction of the air flow flowing through the air intake passage, or in a side face on a rear side of the housing relative to the gas flowing through the air intake passage, the gas intake port includes a plurality of gas intake ports, the plurality of gas intake ports are provided on the side face of the housing along the direction of the gas flowing through the air intake passage.

\* \* \* \* \*